United States Patent
Astratov et al.

(10) Patent No.: US 9,835,870 B2
(45) Date of Patent: Dec. 5, 2017

(54) SUPER-RESOLUTION MICROSCOPY METHODS AND SYSTEMS ENHANCED BY DIELECTRIC MICROSPHERES OR MICROCYLINDERS USED IN COMBINATION WITH METALLIC NANOSTRUCTURES

(71) Applicants: Vasily N. Astratov, Charlotte, NC (US); Nicholaos I. Limberopoulos, Dayton, OH (US); Augustine M. Urbas, Oakwood, OH (US)

(72) Inventors: Vasily N. Astratov, Charlotte, NC (US); Nicholaos I. Limberopoulos, Dayton, OH (US); Augustine M. Urbas, Oakwood, OH (US)

(*) Notice: Subject to any disclaimer, the term of this patent is extended or adjusted under 35 U.S.C. 154(b) by 13 days.

(21) Appl. No.: 15/172,703

(22) Filed: Jun. 3, 2016

(65) Prior Publication Data
US 2016/0357026 A1    Dec. 8, 2016

Related U.S. Application Data

(60) Provisional application No. 62/171,438, filed on Jun. 5, 2015.

(51) Int. Cl.
*G02B 27/58* (2006.01)
*G02B 5/00* (2006.01)
(Continued)

(52) U.S. Cl.
CPC ............ *G02B 27/58* (2013.01); *G01N 21/01* (2013.01); *G01N 21/17* (2013.01); *G02B 5/008* (2013.01);
(Continued)

(58) Field of Classification Search
CPC ........ G02B 5/008; G02B 21/32; G02B 27/58; G03F 1/50; G03F 1/54; G01N 21/01;
(Continued)

(56) References Cited

U.S. PATENT DOCUMENTS 7,279,253 B2 * 10/2007 Yamada ................... G03F 1/50
  430/396
8,181,268 B2 * 5/2012 Nakata ................... B82Y 15/00
  850/22

(Continued)

OTHER PUBLICATIONS

Zengbo Wang et al.; Optical virtual imaging at 50 nm lateral resolution with a white-light nanoscope; Nature Communications / 2:218 / DOI: 10.1038/ncomms1211; Received Aug. 16, 2010, Accepted Jan. 26, 2011, Published Mar. 1, 2011; pp. 1-6; Macmillan Publishers Limited.

(Continued)

*Primary Examiner* — Loha Ben
(74) *Attorney, Agent, or Firm* — Clements Bernard Walker PLLC; Christopher L. Bernard

(57) ABSTRACT

Methods and systems for the super-resolution imaging can make visible strongly subwavelength feature sizes (even below 100 nm) in the optical images of biomedical or any nanoscale structures. The main application of the proposed methods and systems is related to label-free imaging where biological or other objects are not stained with fluorescent dye molecules or with fluorophores. This label-free microscopy is more challenging as compared to fluorescent microscopy because of the poor optical contrast of images of objects with subwavelength dimensions. However, these methods and systems are also applicable to fluorescent imaging. Their use is extremely simple, and it is based on application of the microspheres or microcylinders or, alternatively, elastomeric slabs with embedded microspheres or microcylinders to the objects which are deposited on the surfaces covered with thin metallic layers or metallic nanostructures. The mechanism of imaging involved use of the (Continued)

plasmonic near-fields for illuminating the objects and virtual imaging of these objects through microspheres or microcylinders. These methods and systems do not require use of fragile probe tips and slow point-by-point scanning techniques. These methods and systems can be used in conjunction with any types of microscopes including upright, inverted, fluorescence, confocal, phase-contrast, total internal reflection and others. Scanning the samples can be performed using micromanipulation with individual spheres or cylinders or using translation of the slabs. These methods and systems are applicable to dry, wet and totally liquid-immersed samples and structures.

20 Claims, 6 Drawing Sheets

(51) Int. Cl.
  *G02B 21/32* (2006.01)
  *G01N 21/01* (2006.01)
  *G01N 21/17* (2006.01)
  *B82Y 30/00* (2011.01)
  *B82Y 35/00* (2011.01)

(52) U.S. Cl.
  CPC .............. *G02B 21/32* (2013.01); *B82Y 30/00* (2013.01); *B82Y 35/00* (2013.01); *G01N 2021/1782* (2013.01)

(58) Field of Classification Search
  CPC ...... G01N 21/17; G01N 21/31; G01N 21/658; G01N 33/00; G01N 2021/178; G01N 2021/1782; B82Y 20/00; B82Y 30/00; B82Y 35/00; B32B 2311/02
  USPC ......... 359/241, 244; 422/400, 408; 430/4, 5, 430/396; 356/244, 301, 311, 316
  See application file for complete search history.

(56) References Cited

U.S. PATENT DOCUMENTS

| | | | | |
|---|---|---|---|---|
| 8,339,597 | B2* | 12/2012 | Dal Negro | G01N 21/253 356/301 |
| 8,407,811 | B2* | 3/2013 | Nakata | B82Y 15/00 850/21 |
| 8,635,710 | B2* | 1/2014 | Nakata | B82Y 15/00 850/22 |
| 9,012,207 | B2* | 4/2015 | Blair | B82Y 15/00 422/82.11 |
| 9,513,226 | B2* | 12/2016 | Pang | G01N 21/658 |

OTHER PUBLICATIONS

Xiang Hao et al.; Microsphere based microscope with optical super-resolution capability; Applied Physics Letters 99, 203102 (2011); pp. 203102-1-203102-3; AIP Publishing.

Arash Darafsheh et al.; Optical super-resolution by high-index liquid-immersed microspheres; Applied Physics Letters 101, 141128 (2012); pp. 141128-1-141128-4; the American Institute of Physics.

K. W. Allen et al.; Super-resolution microscopy by movable thin-films with embedded microspheres: Resolution analysis; Ann. Phys. (Berlin) 527, No. 7-8, 513-522 (2015) / DOI 10.1002/andp.201500194; Received Jan. 2, 2015, revised Jul. 16, 2015, Published online Aug. 14, 2015; pp. 513-522; Wiley-VCH Verlag GmbH & Co. KGaA, Weinheim.

Xiang Hao et al.; Far-field super-resolution imaging using near-field illumination by micro-fiber; Applied Physics Letters 102, 013104 (2013); pp. 013104-1-013104-4; AIP Publishing.

Lin Li et al.; Label-free super-resolution imaging of adenoviruses by submerged microsphere optical nanoscopy; Light: Science & Applications (2013) 2, e104; doi:10.1038/lsa.2013.60; Received Aug. 29, 2012; revised Jun. 24, 2013; accepted Jun. 25, 2013; pp. 1-9; published online Sep. 27, 2013.

Hui Yang et al.; Super-Resolution Biological Microscopy Using Virtual Imaging by a Microsphere Nanoscope; small 2013, DOI: 10.1002/smll.201302942; Received: Sep. 11, 2013, Revised: Nov. 13, 2013, Published online, www.small-journal.com; pp. 1-7; 2013 Wiley-VCH Verlag GmbH & Co. KGaA, Weinheim.

Igor Zoric et al.; Gold, Platinum, and Aluminum Nanodisk Plasmons: Material Independence, Subradiance, and Damping Mechanisms; vol. 5, No. 4; Received for review Aug. 26, 2010 and accepted Mar. 25, 2011; Published online Mar. 25, 2011; pp. 2535-2546; American Chemical Society.

* cited by examiner

SUPER-RESOLUTION MICROSCOPY METHODS AND SYSTEMS ENHANCED BY DIELECTRIC MICROSPHERES OR MICROCYLINDERS USED IN COMBINATION WITH METALLIC NANOSTRUCTURES

CROSS-REFERENCE

The present patent application/patent claims the benefit of priority of co-pending U.S. Provisional Patent Application No. 62/171,438, filed on Jun. 5, 2015, and entitled "SUPER-RESOLUTION MICROSCOPY METHODS AND SYSTEMS ENHANCED BY DIELECTRIC MICROSPHERES AND METALLIC NANOSTRUCTURES," the contents of which are incorporated in full by reference herein.

STATEMENT OF GOVERNMENT INTEREST

The United States Government has rights in the present invention pursuant to an employer-employee relationship with some of the inventors as U.S. Air Force Research Laboratory employees or contractors.

FIELD

The present invention relates generally to microscopy methods and systems. More specifically, the present invention relates to super-resolution microscopy methods and systems enhanced by dielectric microspheres or microcylinders used in combination with metallic nanostructures.

BACKGROUND

Super-resolution is introduced in respect to conventional diffraction-limited resolution which is defined as a minimal distance (d) between two point-sources for which two images can be discerned as two separate irradiance maxima. There are several slightly different criteria of such discernibility. The classical diffraction-limited resolution can be represented as $d=K\times\lambda/(NA)$, where K=0.5, 0.61, 0.473, and 0.515. Here, the numerical aperture of the imaging system is represented by $NA=n_o\times\sin\theta$, where $n_o$ is the object-space refractive index and $\theta$ is the half of the objective's acceptance angle. Based on a solid-immersion concept, the top estimate for diffraction-limited resolution can be obtained by assuming that $n_o$ is equal to the highest index in the system which is $n_s$.

It is important to distinguish between the super-resolution in a fluorescent microscopy and in a label-free microscopy. The super-resolution in a fluorescent microscopy is very advanced area of studies. The recent 2014 Nobel prize in Chemistry was awarded "for the development of super-resolved fluorescent microscopy." In the case of fluorescent microscopy, the biological or other objects are stained with fluorescent dye molecules or with the fluorophores. In some cases, brightly fluorescent quantum dots or other nanoscale objects can be used. In this type of microscopy, the actual "object" of imaging such as dye molecule, fluorophore or quantum dot is much smaller than the diffraction limit. This allows obtaining extraordinary detailed information about the object if additional techniques are used. There are many modifications of fluorescent microscopy. In all of these methods, the dye molecules, fluorophores or semiconductor nanocrystals are placed on the target structure by direct labeling techniques. The well-known example of such microscopies includes stimulate emission depletion (STED) method, but there are many other techniques such as photoactivated localization microscopy (PALM) microscopy, fluorescence photoactivation localization microscopy (FPALM), stochastic image reconstruction microscopy (STORM), and other methods using labeling or staining the tissue or samples. The resolution advantage of these methods is rooted in the fact that the actual "objects" are extremely small light sources, usually with dimensions on the scale of few nanometers or even smaller. Combining these small dimensions of the light sources with special types of nonlinear or bleaching effects allows obtaining better than diffraction-limited resolution in the fluorescent microscopy. It also simplifies measurement of the resolution of the system. The irradiance distribution of the image of such "point" objects represents so-called "point-spread function" (PSF). According to a Houston resolution criterion, the width of PSF is equal to the optical resolution of the system. So, measurement of the resolution is relatively simple in fluorescent microscopy because the point-objects are readily available. However, the fluorescence labeling has many disadvantages such as photobleaching and most importantly the need for labeling itself Methods and systems considered in this invention can be realized in combination with fluorescent microscopy, but mainly the proposed methods and systems belong to label-free microscopy.

For high-resolution applications, the label-free microscopy is more challenging and less developed compared to fluorescent microscopy. The ultimate freedom from fluorescent markers constitutes the goal of label-free microscopy. However, removing bright fluorescent objects immediately poses a main problem of the label-free microscopy—its low-contrast imaging mechanisms. Usually, the imaging is provided due to relatively weak light scattering mechanisms. Reduction of the size of the objects in the label-free microscopy makes them difficult to see. This means that it is challenging to discern small-scale objects on the background level of illumination inevitably presenting in microscopy. Another problem is that the measurement of the resolution becomes to be much harder problem in the label-free microscopy compared to the fluorescent microscopy. The textbook definitions of the optical resolution are made for idealized point sources. However, if the object is sufficiently small, it is not visible in the label-free microscopy. Generally, it means that more complicated methods of analysis of resolution based on images of finite-size objects are required in this area.

The approach to super-resolution imaging is based on using the optical near-fields since such fields can carry out very detailed information about the object. The problem is that the optical near-fields exponentially decay at very short distances (on the order of $\sim\lambda/2$) from the object.

The near-field scanning optical microscopy (NSOM) gets around this problem in a complete and general way. The key point is that the photonic probe with a nanoscale hole in the metallic aperture or plasmonic probe with the nanoscale diameter is placed at very close distances from the object, where the non-propagating evanescent fields dominate. The resolution on the order of $\sim$20 nm can be obtained by NSOM, however only by the expense of the transmitted intensity. The attenuation of the transmission to $\sim 10^{-5}$–$10^{-6}$ is quite common for NSOM, especially for the smallest probe apertures. In addition, the probe can be easily damaged by the contact with the surface, and it needs sophisticated and precise setup for the sample surface scanning.

More recent and advanced approach to super-resolution imaging is based on using super-oscillatory lens. The ability to focus beyond the diffraction limit is related to the fact that band-limited functions are able locally to oscillate arbitrarily quickly, faster than their highest Fourier components, a phenomenon now known as super-oscillation. The resolution on the order o~λ/6 has been claimed based on a discernibility of certain features in the optical images of these structures. It should be noted that more rigorous resolution treatment would require a convolution with the point-spread function. The limitations of this method are connected with a need in extremely precise fabrication and characterization equipment which is not likely to be available outside the leading research laboratories.

Another method of improving the resolution is based on illumination provided by the evanescent fields. However, for objects with complex shape, the use of this technique is not straightforward and it requires complicated image recovery algorithms which would make this method impractical in such cases.

One of the approaches to label-free super-resolution is based on using properties of plasmon-polaritons in metallo-dielectric structures, namely the property that they have much shorter wavelength compared to light waves with the same frequency propagating in air. This means that the plasmon-polaritons can carry out much more detailed spatial information about the object compared to conventional diffraction-limited optics. The idea of building super-resolution device is to provide a certain magnification of the image of the object using a plasmon-polariton medium (or a plasmon-polariton lens) where the detailed information about the object is preserved. The magnified image can be viewed by a conventional diffraction-limited microscope; however the information about the object details beyond the diffraction limit will be still observable due to the magnification provided by the plasmon-polariton medium. The limitations of this approach is that it works in a narrow range of frequencies, requires challenging fabrication, and it is usually applicable only for in-plane propagation of light.

Another approach is based on using far-field hyperlens. The hyperlens utilizes cylindrical or spherical geometry to magnify the subwavelength features of imaged objects so that these features are above the diffraction limit at the hyperlens output. Thus, the output of the hyperlens consists entirely of propagating waves, which can be processed by conventional optics. Near-field plasmonic super-lenses and 3D hyperlenses have been demonstrated with resolutions λ/3.6 and λ/2.6, respectively. These systems operate in narrow spectral ranges and are very difficult to fabricate. More recently, a non-resonant hyperlens was demonstrated in visible. It should be noted, however, that hyperlenses developed in all these works require a challenging fabrication. Most importantly, they are difficult to use with the objects which are not fabricated inside the imaging device. This means that the practical use of these structures for imaging biological and other similar samples is very limited at present time.

There are other methods of creating label-free contrasts in microscopy based on the harmonic generation of the illumination or four-wave mixing processes through the non-linear response of the sample. For instance, it has been shown that collagen can be nicely imaged through second harmonic generation (SHG).

In this regard, imaging by dielectric microspheres or microcylinders emerged as a surprisingly simple way of obtaining super-resolved images of nanoscale structures. The method implies bringing a dielectric microsphere in a contact position with investigated structure, so that the microsphere experiences the object's optical near-field and creates a magnified virtual image that can be viewed by a standard microscope at a certain depth inside the structure. Initially, the method has been demonstrated for micron-scale low-index ($n_s$=1.46) silica spheres in air. At that time, it has been proposed that this technique would not work for high-index ($n_s$>1.8) spheres as well as for spheres totally immersed in a liquid. So, the proposal to use high-index spheres totally submersed in a liquid or embedded inside elastomeric slabs was counterintuitive and inventive. Later, it was demonstrated that it was this proposal that turned out to be the most useful method for imaging biomedical samples. The label-free super-resolution microscopy has been realized for imaging of adenoviruses and mitochondria using liquid-immersed high-index microspheres. The fluorescent imaging through microspheres has been realized for stained biological structures.

BRIEF SUMMARY

This invention is devoted to methods and systems of super-resolution imaging of nanoscale structures with the resolution beyond the diffraction limit. The main application of the proposed method and systems is related to a label-free imaging where the biological or other objects are not stained with fluorescent dye molecules or with the fluorophores. The label-free microscopy is more challenging compared to fluorescent microscopy because of the poor optical contrast of images of objects with subwavelength dimensions. However, the proposed methods and systems are also applicable in combination with fluorescent microscopy. The advantage of the proposed methods and systems is increased optical contrast and resolution of ultra-small objects. The proposed approach includes the use of micro spheres or microfibers placed in contact or near-contact positon with the object of studies. In contrast to a previous work devoted to imaging by microspheres, the physical mechanism of the proposed methods and systems includes a resonant or non-resonant enhancement of plasmonic near-fields in the vicinity of the objects of studies. This is achieved by using specially designed surface metallic nanostructures. The geometrical parameters of the metallic nanostructures are engineered to provide a strong resonant or non-resonant enhancement of the plasmonic near-fields at the illumination wavelengths of the external microscope system. This design is based on using surface plasmon polaritons in thin metallic films or localized surface plasmon resonances in the patterned metallic nanostructures. In the latter case, the spectral shift of localized surface plasmon resonances depends on size-quantization or other effects in metallic nanostructures. In some of the designs, the characteristic feature sizes of the surface nanostructures are too small to be resolved, however the resonant enhancement of the plasmonic near-field produced by this nanostructure can facilitate super-resolution imaging of nanoscale objects through the dielectric microspheres or microfibers. The resolution advantage takes place due to simultaneous presence of the optical near-fields in the illumination and the image magnification properties of dielectric microspheres and microcylinders. For this reason, the detailed spatial information about the object can be preserved in the virtual image. Since such image is observed by the microscope objective in the far-field, it has a diffraction-limited resolution. However, due to the magnification of the system which takes place for extremely small object's features acquired with participation of its near-fields, the resulting resolution of the system can exceed the classical diffraction limit.

Another possibility offered by the methods and systems proposed in this patent is based on structured illumination of the object which can additionally increase the resolution. The spatial configuration of the coupled nanoplasmonic modes excited in such arrays is strongly dependent on the illumination wavelength. By changing the illumination wavelength, various illumination patterns can be realized. The corresponding images can be combined and processed collectively to increase the resolution of the images. The advantage provided by the structured illumination is well known. In this invention, we propose to use this advantage specifically in the case of microsphere-assisted imaging of objects illuminated by nanoplasmonic arrays. In this case, all advantages (near-field illumination, magnification involving near-fields and structured illumination), take place simultaneously that can result in further increase of the resolution.

The proposed methods and systems for super-resolution imaging can be realized in four embodiments. In the first embodiment, the super-resolution imaging is provided using relatively low index ($n_s$~1.4-1.6) spheres or cylinders without their submersion in a liquid. In the second embodiment, the super-resolution imaging is provided using high-index ($n_s$>1.8) spheres or cylinders totally submersed in a liquid. In the third embodiment, the super-resolution imaging is provided using elastomeric slabs with embedded high-index spheres or cylinders. Such slabs were recently developed without using nanoplasmonic arrays for illumination purposes. In the fourth embodiment, the spheres can be micromanipulated by using a stick or a microfiber in air or in liquid environment. In the fifth embodiment, the spheres or cylinders are semi-embedded in slabs. Such structures can be micromanipulated in a liquid environment by moving the entire slab. In all embodiments, the dielectric microspheres or microcylinders are placed in a contact or near-contact position with the investigated nanoscale objects in such a way that the object of study experiences plasmonic near-fields either due to excitation of plasmon polaritons in thin metallic films or due to resonant excitation of localized plasmons in the patterned metallic arrays. All embodiments use a microscopy setup or a visual inspection system which are represented by upright, inverted, fluorescence, confocal, total internal reflection (TIRF), phase contrast, structured illumination (SIM), saturated emission depletion (STED), localization microscopy such as STORM and PALM as well as super-resolved optical fluctuation imaging (SOFI) or any other type of system for observation of the virtual images of nanoscale objects through the microsphere or microcylinder. The methods and systems proposed in this invention can be realized using spheres or cylinders with diameters varying from several wavelengths (~1-2 μm in visible) up to thousands of wavelengths.

DETAILED DESCRIPTION

Figure 1:
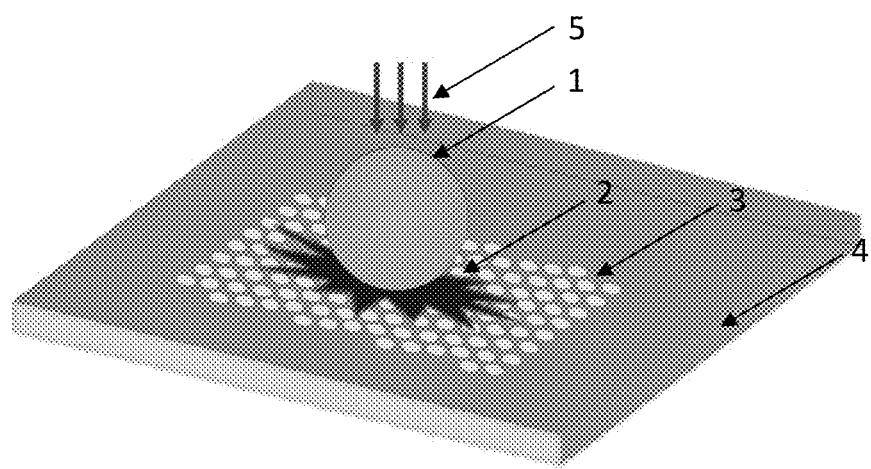
FIG. 1. The first embodiment of the proposed methods and systems: 1-dielectric microsphere with the index in the 1.4-1.6 range, 2-investigated sample, 3-metallic nanostructure, 4-substrate, 5-microscope illumination.

The present invention now will be described more fully hereinafter in the following detailed description of the invention, in which some, but not all embodiments of the invention are described. Indeed, this invention may be embodied in many different forms and should not be construed as limited to the embodiments set forth herein; rather, these embodiments are provided so that this disclosure will satisfy applicable legal requirements.

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In some embodiments, this invention is aimed at achieving label-free super-resolution imaging of biomedical or other structures with improved resolution and contrast. The key concept underlying this invention is that in order to achieve these goals, one should find a way to enhance the optical near-fields used for illuminating the object. In this invention, we propose to use metallic nanostructures in close vicinity to the object of studies to provide such illumination.

The metallic nanostructures support either surface plasmon polaritons, if they are continuous thin films, or localized surface plasmon resonances (LSPRs), if they are patterned to produce metallic islands or periodical arrays. Both types of surface electromagnetic excitations can be used for improving imaging because each of them is characterized with a strong optical near-fields in the vicinity of the metallic film. However, the excitation of LSPRs is especially advantageous for this purpose. If the microscope illumination system (or additional illumination system) is tuned into LSPR spectral peak, it would produce tremendously enhanced plasmonic near-field in close vicinity to metallic nanostructure. This plasmonic near-field would penetrate the object of study providing bright illumination of the object with the evanescent waves. The evanescent waves carry out very detailed information about the object, much more detailed than the diffraction limit. Such evanescent fields are coupled to dielectric microsphere or microcylinder which forms a magnified virtual image of the object. The virtual image can be observed in the far-field by using a microscope or any other imaging system with the diffraction-limited resoluton. However, since this image is magnified, it actually carries information about the features of the object smaller than the diffraction limit.

Another possible mechanism of super-resolution is related to imaging of the objects formed by nanoscale pieces separated by the nanoscale gaps. Due to the optical coupling between the pieces, the coupled optical modes are formed in such objects. Such coupled optical modes can play a role of the optical antenna, radiating or scattering light into the microscope objective. This can produce extraordinary well-resolved images where the object's features much smaller than the diffraction limit can be visualized. The role of metallic thin films or arrays consists in creating a strong near-field plasmonic illumination for such objects which facilitate excitation of coupled optical modes in such objects.

The first embodiment of the proposed methods and systems is illustrated in FIG. 1. In order to project the image in the far-field we propose to use a previously developed technology of imaging through the microspheres or cylinders. (Only the case of a micro sphere is illustrated in FIG. 1). The proposed technology is expected to work for objects with the thickness limited by the wavelength of light. The microsphere or microcylinder the relatively small index of refraction ($n_s$~1.4-1.6) is placed above the object, so that its surface is located in near-field vicinity to the metallic nanostructure fabricated on the surface of the substrate. The object can be in a dry form or it can contain some amount of liquid, however the spheres or cylinders are not totally covered with liquid. Many biomedical and nanotechnology objects can be accommodated between the metallic nanostructure and the surface of microspheres or microcylinders. The examples include cells, viruses, proteins, carbon nanotubes, clusters of molecules, et al. All these objects have dimensions smaller than the wavelength of light. Slight scattering of plasmonic near-fields by the objects can be used for their imaging through the microspheres or microcylinders. Using this embodiment, we can also visualize the fluorescent objects. In the latter case, we can either provide excitation of emission due to plasmonic near-fields or we can enhance the emission properties of investigated species by coupling emitted light to plasmonic near-fields. In both cases, coupling to plasmonic excitations would facilitate better spatial resolution due to coupling of light into microspheres or microcylinders and due to the image magnification effect provided by such contact microlenses. One more resource is offered by structured illumination of the object which can be realized by using different illumination wavelengths producing various illumination patterns. On the other hand, in the case of continuous metallic films, it is possible to couple light to surface plasmon-polariton excitations. They can also produce illumination of the object with the plasmonic near-fields.

Figure 2:
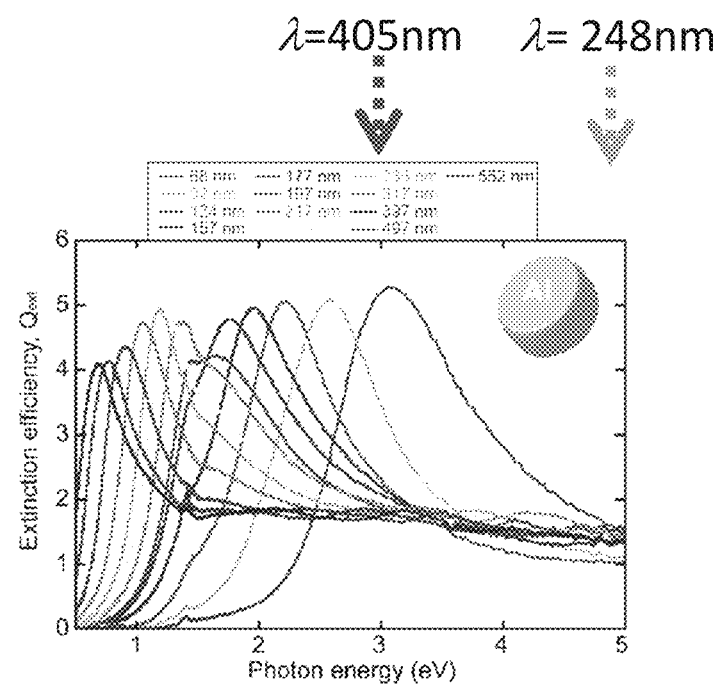
FIG. 2. Extinction efficiency meaning the efficiency of excitation of localized surface plasmon resonances. The diameters of Al cylinders are represented by different colors. The positions of illumination at λ=405 nm and λ=248 nm are indicated.

As illustrated in FIG. 2, the spectral position of LSPR is dependent on the feature sizes of metallic nanostructure. There are many possibilities of fabrication of such metallic nanostructures. It can be formed by metallic building blocks shaped as circles, squares or other shapes. They can be arranged as triangular, square, quazi-periodic or other types of 2D lattices. In order to produce relatively uniform evanescent field distribution, the gaps between the building blocks should not be too large. On the other hand, in order to provide well-pronounced resonances in the individual building blocks, the gaps should be sufficiently large compared to the plasmonic wavelength. As an example, if the plasmonic wavelength is on the order of 20 nm, the separation between the building blocks in the 20-50 nm range seems to be a good tradeoff The results in FIG. 2 illustrate an example of LSPRs in aluminum disks with 20 nm. Based on these results, it can be suggested that if the microscope illumination is provided at $\lambda$=405 nm, a strong resonance is expected for the cylinder diameters about 68 nm. By extrapolating the presented dependencies to shorter wavelengths, it can be anticipated that in the case of illumination with the deep-UV wavelength $\lambda$=248 nm, a strong resonance would be observable in Al cylinders with diameters in the 20-40 nm range. It is important to note that such cylinders are too small to be observed directly, but they would produce extremely strong evanescent field which will provide bright illumination of the objects.

Figure 3:
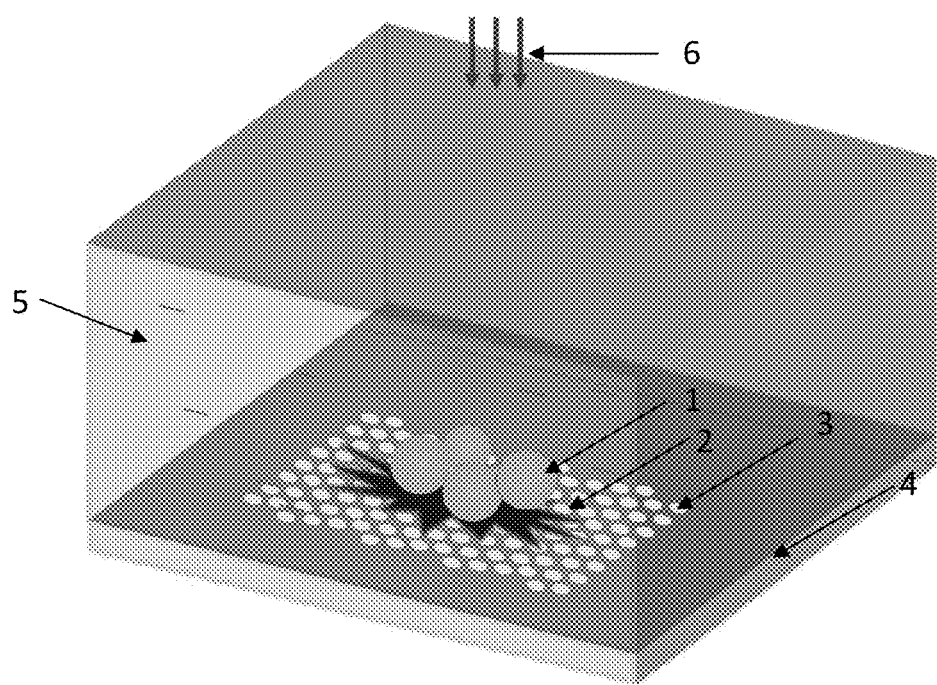
FIG. 3. The second embodiment of the proposed systems and methods: 1-dielectric microspheres with the index>1.8, 2-investigated sample, 3-metallic nanostructure, 4-substrate, 5-liquid, 6-microscope illumination.

The second embodiment of the proposed methods and systems is illustrated in FIG. 3. It provides an additional enhancement of the resolution and quality of imaging due to use of liquid-immersed high-index ($n_s$>1.8) microspheres or microcylinders. (Only the case of microspheres is illustrated in FIG. 3). They are totally submersed in a liquid. The height of the liquid is not critically important for the super-resolution imaging. It is particularly suitable for imaging biomedical structures since they are often water-immersed.

Figure 4:
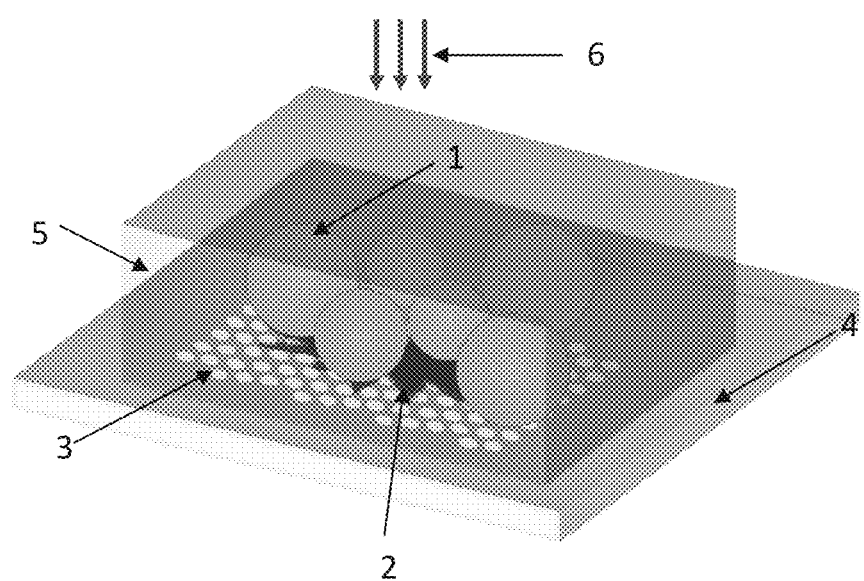
FIG. 4. The third embodiment of the proposed systems and methods: 1-dielectric microspheres with the index>1.8, 2-investigated sample, 3-metallic nanostructure, 4-substrate, 5-transparent elastomeric slab, 6-microscope illumination.

The third embodiment of the proposed methods and systems is illustrated in FIG. 4. It provides an additional flexibility due to large number of microspheres or microcylinders with different diameters and, potentially, made from different materials, which are embedded in transparent flexible elastomeric slabs. (Only the case of microspheres is illustrated in FIG. 4). The spheres are held in nanometer-scale proximity to the bottom surface of the slabs or "coverslips", Once the coverslip is attached to a nanoplasmonic structure, the tips of microspheres can experience the object near-fields leading to the possibility of super-resolution imaging. Each sphere has a field-of-view on the order of a quarter of its diameter. Multiple spheres allow inspecting larger area of the sample. Most importantly, the entire films can be controllably shifted along the sample providing the surface scanning functionality.

Figure 5:
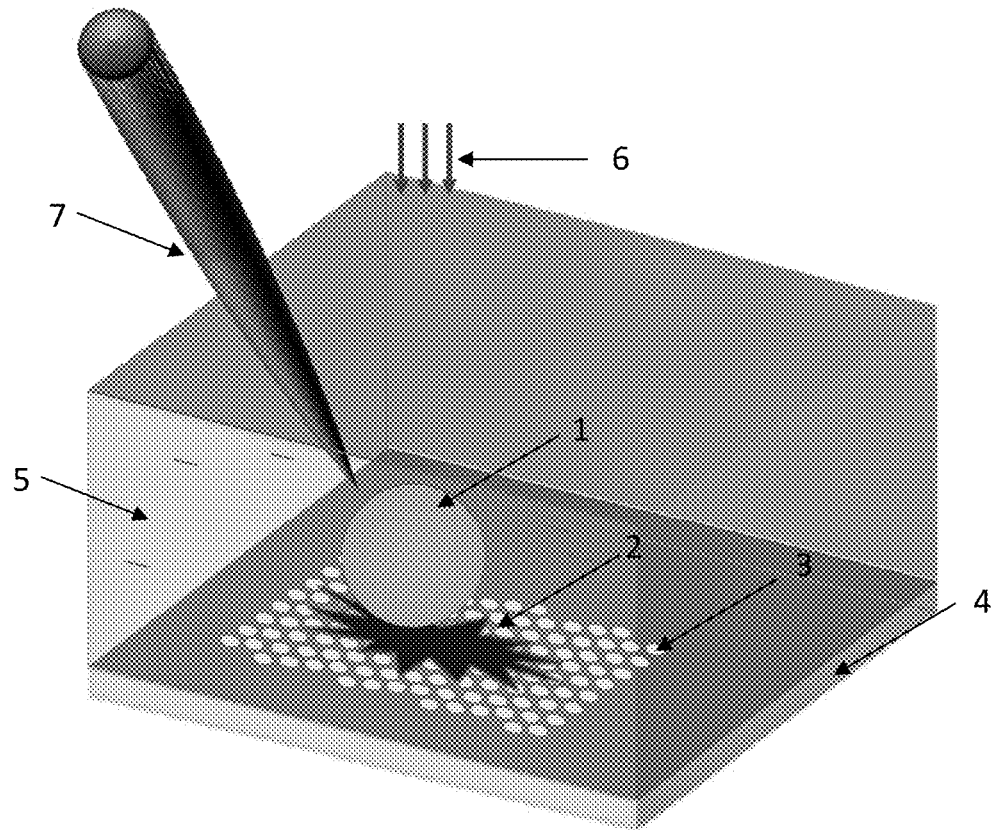
FIG. 5. The fourth embodiment of the proposed systems and methods: 1-dielectric microspheres which can have low-index ($n_s$~1.4-1.6) in air or high-index ($n_s$>1.8) in a liquid environment (the latter case is illustrated in this figure), 2-investigated sample, 3-metallic nanostructure, 4-substrate, 5-liquid, 6-microscope illumination, 7-micromanipulation stick.

The fourth embodiment of the proposed methods and systems is illustrated in FIG. 5. (Only the case of a microsphere is illustrated in FIG. 5). The microsphere or microcylinder can be micromanipulated into a contact position with the investigated nanoscale objects. In this sense, the microsphere or microcylinder becomes a local imaging probe for reaching any areas on the substrate surface. This embodiment can be realized using relatively low-index spheres (ns~1.4-1.6) or cylinders if the manipulation and imaging are provided in air environment. It can be also realized with high-index ($n_s$>1.8) spheres or cylinders immersed in a liquid, as illustrated in FIG. 5. The latter case is particularly suitable for imaging biomedical structures since they are often water-immersed. The micromanipulation can be achieved by different techniques. The microsphere can be attached to a tapered microfiber which can be controlled by micromanipulators. Alternatively, it can be controlled by the additional optical tweezers setup or otherwise. The microcylinder can be realized by etching the fiber. In the latter case, the micromanipulation can be simplified since the cylindrical lens used for imaging is obtained from the same piece of fiber which can be mechanically micromanipulated.

Figure 6:
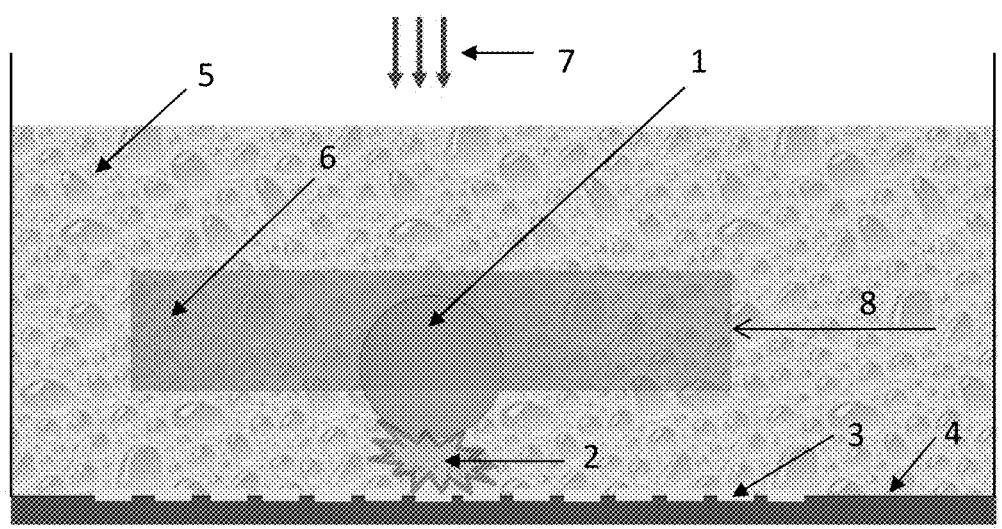
FIG. 6. The fifth embodiment of the proposed systems and methods: 1-dielectric microspheres with the index>1.8, 2-investigated sample, 3-metallic nanostructure, 4-substrate, 5-liquid, 6-transparent elastomeric slab, 7-microscope illumination, 8-micromanipulation of the slab.

The fifth embodiment of the proposed methods and systems is illustrated in FIG. 6. In this embodiment, the high-index ($n_s$>1.8) spheres or cylinders are semi-embedded (or partly embedded) in a transparent slab. (Only the case of a microsphere is illustrated in FIG. 6), This embodiment has two advantages for practical use in biomedical imaging, First, instead of manipulating with individual spheres which are rather small, it makes possible to controllably translate the entire slab which is much easier to handle and connect to micromanipulators. Second, it is ultimately suitable for visualizing samples in a liquid form. In comparison with the third embodiment in FIG. 4, it does not require good physical contact between the slab and the sample surface. Since the microspheres are extended from the slab, only the tips of the microspheres reach close to contact positions with the objects deposited at the substrate. This can be easily realized in a liquid environment with applying only little downward force on the slab.

What is claimed is:

1. A super-resolution optical imaging method, comprising:
    providing a sample to be optically imaged;
    disposing one or more microstructures substantially adjacent to the sample to be optically imaged;
    disposing a metallic nanostructure substantially adjacent to the sample to be optically imaged, wherein the metallic nanostructure is operable for enhancing plasmonic near-fields at selected illumination wavelengths; and
    imaging the sample with the metallic nanostructure present.

2. The super-resolution optical imaging method of claim 1, wherein imaging is performed with one of an upright, inverted, fluorescence, confocal, total internal reflection (TIRF), phase contrast, structured illumination (SIM), saturated emission depletion (STED), localization microscopy (STORM or PALM), super-resolved optical fluctuation imaging (SOFI), or other microscope system.

3. The super-resolution optical imaging method of claim 1, wherein the microstructures comprise relatively low-index ($n_s$~1.4-1.6) spheres or cylinders if the manipulation and imaging are provided in an air environment.

4. The super-resolution optical imaging method of claim 1, wherein the microstructures comprise relatively high-index ($n_s$>1.8) spheres or cylinders if the manipulation and imaging are provided in a liquid environment.

5. The super-resolution optical imaging method of claim 1, wherein the microstructures comprise spheres or cylinders that are connected to microfiber probes, translational stages or other micromanipulation tools to control their position.

6. The super-resolution optical imaging method of claim 1, wherein the microstructures comprise spheres or cylinders that are positioned using optical tweezers.

7. The super-resolution optical imaging method of claim 1, wherein the microstructures comprise transparent slabs containing relatively high-index ($n_s$>1.8) spheres or cylinders that are completely embedded in the slabs substantially adjacent to a surface of the slabs.

8. The super-resolution optical imaging method of claim 1, wherein the microstructures comprise transparent slabs with partially embedded relatively high-index ($n_s$>1.8) spheres or cylinders.

9. The super-resolution optical imaging method of claim 1, wherein the metallic nanostructure comprises a thin layer of metal with surface plasmon polariton electromagnetic excitations.

10. The super-resolution optical imaging method of claim 1, wherein the metallic nanostructure comprises a periodic or nonperiodic array supporting localized surface plasmon resonances.

11. A super-resolution optical imaging system, comprising:
    one or more microstructures disposed substantially adjacent to a sample to be optically imaged;
    a metallic nanostructure disposed substantially adjacent to the sample to be optically imaged, wherein the metallic nanostructure is operable for enhancing plasmonic near-fields at selected illumination wavelengths; and
    a microscope system for imaging the sample with the metallic nanostructure present.

12. The super-resolution optical imaging system of claim 11, wherein the microscope system comprises one of an upright, inverted, fluorescence, confocal, total internal reflection (TIRF), phase contrast, structured illumination (SIM), saturated emission depletion (STED), localization microscopy (STORM or PALM), super-resolved optical fluctuation imaging (SOFI), or other microscope system.

13. The super-resolution optical imaging method of claim 11, wherein the microstructures comprise relatively low-index ($n_s$1.4-1.6) spheres or cylinders if the manipulation and imaging are provided in an air environment.

14. The super-resolution optical imaging method of claim 11, wherein the microstructures comprise relatively high-index ($n_s$>1.8) spheres or cylinders if the manipulation and imaging are provided in a liquid environment.

15. The super-resolution optical imaging method of claim 11, wherein the microstructures comprise spheres or cylinders that are connected to microfiber probes, translational stages or other micromanipulation tools to control their position.

16. The super-resolution optical imaging method of claim 11, wherein the microstructures comprise spheres or cylinders that are positioned using optical tweezers.

17. The super-resolution optical imaging method of claim 11, wherein the microstructures comprise transparent slabs containing relatively high-index ($n_s$>1.8) spheres or cylinders that are completely embedded in the slabs substantially adjacent to a surface of the slabs.

18. The super-resolution optical imaging method of claim 11, wherein the microstructures comprise transparent slabs with partially embedded relatively high-index ($n_s$>1.8) spheres or cylinders.

19. The super-resolution optical imaging method of claim 11, wherein the metallic nanostructure comprises a thin layer of metal with surface plasmon polariton electromagnetic excitations.

20. The super-resolution optical imaging method of claim 11, wherein the metallic nanostructure comprises a periodic or nonperiodic array supporting localized surface plasmon resonances.

* * * * *